United States Patent
Ranieri et al.

(10) Patent No.: US 8,160,817 B2
(45) Date of Patent: Apr. 17, 2012

(54) METHOD FOR DETERMINING THE RESISTANCE OF THE RESPIRATORY SYSTEM OF A PATIENT

(75) Inventors: Marco Ranieri, Turin (IT); Cosimo Micelli, Bari (IT); Lorenzo Appendini, Meina (IT)

(73) Assignee: Dräger Medical GmbH, Lübeck (DE)

( * ) Notice: Subject to any disclaimer, the term of this patent is extended or adjusted under 35 U.S.C. 154(b) by 1069 days.

(21) Appl. No.: 12/048,380

(22) Filed: Mar. 14, 2008

(65) Prior Publication Data
US 2008/0234595 A1    Sep. 25, 2008

(51) Int. Cl.
*G01N 33/48*  (2006.01)
*G01N 33/50*  (2006.01)
*G06F 17/50*  (2006.01)

(52) U.S. Cl. ....................................................... 702/19

(58) Field of Classification Search .................. None
See application file for complete search history.

(56) References Cited

OTHER PUBLICATIONS

R. Kuhlen et al., A Method for PO.1 "Measurement Using Standard Respiratory Equipment", Intensive Care Med., Jul. 21, 1995: 545-546.

Younes et al., "A Method for Non-invasive Determination of Inspiratory Resistance During Proportional Assist Ventilation", Am. J. Respir. Crit. Cate Med. 2001; 163: 829-839.

Younes et al., "A Method for Measuring Passive Elastance During Proportional Assist Ventilation", Am. J. Respir, Crit. Care Med. 2001; 164: 50-60.

*Primary Examiner* — Jason Sims
(74) *Attorney, Agent, or Firm* — McGlew and Tuttle, P.C.

(57) ABSTRACT

A method for automatically determining the resistance of the respiratory system of a spontaneously breathing intubated patient. The method includes measuring flow (V') and airway pressure (Paw)) as a function of time; determining the airway pressure at the end of the occlusion period as end of occlusion airway pressure Paw(tc)=Poccl; analyzing a time 5 dependence of the flow starting at the end of the occlusion period to determine a transition time td at which the slope of the flow changes from a first high value to a second lower value; determining the flow at the transition time as transition time flow V'(td)=V'peak and determining the airway pressure at the transition time as transition time pressure Paw(td); and calculating the resistance on the basis of the ratio of an estimated driving pressure at the transition time Pdrv(td) and the transition time flow V'peak.

19 Claims, 3 Drawing Sheets

METHOD FOR DETERMINING THE RESISTANCE OF THE RESPIRATORY SYSTEM OF A PATIENT

CROSS REFERENCE TO RELATED APPLICATIONS

This application claims the benefit of priority under 35 U.S.C. §119 of European Patent Application EP 07 005 690.8 filed Mar. 20, 2007, the entire contents of which are incorporated herein by reference.

FIELD OF THE INVENTION

The present invention relates to a method for automatically determining the resistance of the respiratory system of a spontaneously breathing, intubated patient, wherein the method is conducted with or without assisted ventilation and includes an occlusion period at the start of inspiration.

BACKGROUND OF THE INVENTION

A method including an occlusion period at the start of inspiration to measure the (negative) inspiratory pressure at the end of a 0.1 second occlusion period is described in R. Kuhlen et al., "*A New Method For P 0.1 Measurement Using Standard Respiratory Equipment*", Intensive Care Med., 1995 July 21: 545-546.

Proportional assist ventilation (PAV/PPS) is a recent mode of ventilatory assistance. In PAV/PPS mode, the ventilator (also known as respirator) generates pressure at the airway opening in proportion to inspiratory flow (flow assist: FA) and to volume (volume assist: VA), both produced by the contraction of the patient's inspiratory muscles. In PAV/PPS mode, the ventilator operates as a servo-system aimed to reduce selectively the elastic and resistive inspiratory workload. Theoretically, the resistance and elastance of the respiratory system should be known exactly to set adequate levels of PAV/PPS. This implies the use of invasive measurements in spontaneously breathing patients, and sedation or sedation/paralysis in mechanically ventilated patients. The lack of any easy technique to measure the patient respiratory mechanics has been recognized as a major problem for the widespread application of PAV/PPS in the clinical environment.

Recently, it has been suggested by Younes et al. ("*A Method for Non-invasive Determination of Inspiratory Resistance During Proportional Assist Ventilation*", Am. J. Respir. Crit. Care Med. 2001; 163: 829-839) that simple maneuvers performed non-invasively during PAV/PPS, might be useful in estimating inspiratory resistance and passive elastance of the respiratory system, see Younes et al. "*A Method for Measuring Passive Elastance During Proportional Assist Ventilation*", Am. J. Respir. Crit. Care Med. 2001; 164: 50-60. In particular, inspiratory resistance may be computed performing repeated brief reductions in airway pressure $P_{aw}$ in the early part of the inflation phase. Airway pressure $P_{aw}$, flow V' and inspiratory volume V are measured at the beginning of the pulse (T0), at the trough of the pulse (T1), and at a point 0.1 seconds before T0 (T1). Equations of motion of the form $P_{mus}+P_{aw}=V'\cdot K_1+V'^2\cdot K_2+V\cdot E$ are generated for the data at the three time points (E=elastance, $K_1$ and $K_2$ are the so-called Rohrer's constants). These three equations can be solved for $K_1$ and $K_2$ if it is arranged that the pulse has an appropriate configuration and timing, and if it is assumed that $\Delta P_{mus}/\Delta T$ is constant for the brief pulse period. This method implies a lot of assumptions and simplifications as well as potential sources of error. Among the latter, the errors related to the extrapolation of the $P_{mus}$ trajectory are potentially the most serious, particularly when respiratory drive and, hence, the rate of rise of $P_{mus}$ are high. As a matter of fact, the rate of growth of $P_{mus}$ during the rising phase in humans is not constant. The passive elastance can be estimated during PAV/PPS by performing a short (0.25 second) end-inspiratory occlusion (EIO), see the second of the above-referenced articles. In these articles it is suggested that $P_{mus}$ declines to 0 during the end-inspiratory occlusion (EIO), a fact that allows $P_{aw}$ to reach a plateau. The value of $P_{mus}$ at the plateau should reflect passive recoil at the prevailing volume. However, also in this case, some problems can limit the accuracy of the measurement. Among them are possible patient reactions to the occlusion or a prolonged $P_{mus}$ decay, and the fact that passive recoil during EIO includes intrinsic positive end expiratory pressure (PEEPi) that has to be taken into account. A further disadvantage of the described method is the measurement of the resistance in the expiration phase, whereas the resistance value is needed for PAV in the inspiration phase. Occlusion (up to 300 ms) at the end of inspiration is rather disturbing for the patients.

SUMMARY OF THE INVENTION

Accordingly, there is a need to provide a method for determining the resistance of the respiratory system in a reliable manner. Furthermore, the method should not or should only minimally affect the breathing activity of the patient.

According to the present invention a method for automatically determining the resistance of the respiratory system of a spontaneously breathing intubated patient is provided, wherein the method is conducted with or without assisted ventilation and includes an occlusion period at the start of inspiration. The method comprises:

measuring flow (V') and airway pressure ($P_{aw}$) as a function of time;

determining the airway pressure at the end ($t_c$) of the occlusion period as end of occlusion airway pressure $P_{aw}(t_c)=P_{occl}$;

analyzing the time dependence of the flow starting at the end of the occlusion period to determine a transition time $t_d$ at which the slope of the flow changes from a first high value to a second lower value, and/or analyzing the time dependence of the airway pressure starting at the end of the occlusion period to determine a transition time $t_d$ at which the slope of the airway pressure changes from a first high value to a second lower value, or by detecting an increase of the airway pressure over a predetermined threshold value to determine the transition time $t_d$;

determining the flow at the transition time as transition time flow $V'(t_d)=V'_{peak}$ and determining the airway pressure at the transition time as transition time pressure $P_{aw}(t_d)$; and calculating the resistance on the basis of the ratio of an estimated driving pressure at the transition time $P_{drv}(t_d)$ to the transition time flow $V'_{peak}$, wherein the value of the transition time driving pressure $P_{drv}(t_d)$ is calculated as sum of the transition time airway pressure $P_{aw}(t)$ and the muscular effort $P_{mus}(t_d)$ at the transition time, which muscular effort $P_{mus}(t_d)$ is extrapolated based on a predetermined time dependence of $P_{mus}(t)$ during the occlusion, and based on the value of the end of occlusion airway pressure $P_{occl}$.

As usual, $P_{mus}$ is used to designate the muscular pressure, $P_{aw}$ designates the airway pressure, wherein the airway pressure (as measured on the Y-piece of the breathing apparatus) is, during an assisted ventilation phase, the pressure provided by the ventilator, i.e. $P_{aw}=VA\cdot V+FA\cdot V'$, and is, during an occlusion period, the pressure created by the muscular breathing effort of the patient. The sum of $P_{mus}$ and $P_{aw}$ is denoted as driving pressure $P_{drv}$. An occlusion designates a period in which the flow is forced to be 0 by a closure of the breathing system.

In the method according, to the invention, flow and airway pressure are measured as functions of time. In the initial occlusion period at the beginning of the inspiration cycle, the muscular inspiratory effort of the patient leads to a decreasing (negative) airway pressure. At the end of the occlusion period a certain pressure is built up, generally referred to as $P_{occl}$ herein. The occlusion period may for example be a period of 0.1 seconds, in which case $P_{occl}$ is normally designated as $P_{0.1}$. After releasing the occlusion, the time dependence of the flow starting at the end of the occlusion period is analyzed to determine a transition time at which the slope of the flow (as a function of time) changes from a first, essentially constant high value to a second lower slope of essentially constant value. The flow at the transition time and the airway pressure at the transition time are determined. The resistance of the respiratory system is calculated on the basis of the ratio of the estimated driving pressure (which can for example be approximated by the difference between the transition time airway pressure and the end of occlusion airway pressure) to the transition time flow. This allows a reliable and rather precise determination of the resistance of the respiratory system since at the beginning of the inspiration phase, just after the initial occlusion, the relation between flow and pressure is dominated by the resistive contribution, or in other words the elastic contribution is, in this initial phase, still negligible. According to the present invention this initial, resistance dominated phase is identified by analyzing the time dependence of the flow and by identifying the transition point of the flow or, airway pressure where a first linear portion of high slope of flow or pressure is transitioning to a second portion of lower slope or where a certain threshold of the airway pressure is reached.

The transition time may for example be determined by fitting a pre-determined non-linear function to the time dependent flow or pressure data, wherein the predetermined non-linear function has a first essentially linear portion and a second essentially linear portion with a smooth transition in between wherein the slopes of the linear portions and the location of the smooth transition are determined by parameters which are varied in the fitting procedure. Alternatively, two straight lines may be fitted to the time dependent flow or pressure data, and the intersection of the two straight lines may be determined as the transition time value.

In a preferred embodiment, in the method for automatically determining the resistance R of the respiratory system, a sequence of different transition times is predetermined/selected and for each transition time the corresponding value of the resistance R is determined. This sequence of resistance values, which shows a possible functional dependence on the transition time, is analyzed, and a resistance value is derived from a region of this function where the dependence of the determined resistance values from the transition times is lowest. This ensures that a reliable final transition time is selected and a corresponding resistance value is determined as trade-off between high variability due to occlusion transition effects (at early transition times) and systematic errors due to neglected elastic recoil (at later-transition times).

As a further alternative, the transition time may be determined by a combination of the above described methods.

According to a further aspect of the invention there is provided a method for automatically determining the elastance (E) of the respiratory system of a spontaneously breathing intubated patient, wherein the method is conducted with or without assisted ventilation and includes, an occlusion period at the start of inspiration. The method further comprises:

a) determining the resistance (R) of the respiratory system by conducting the method described above;
b) measuring the inspiratory volume as a function of time;
c) determining the airway pressure $P_{aw}(t)$ during the occlusion period ($t_b<t<t_c$) as a function of time;
d) extrapolating the airway pressure $P_{aw}(t)$ during the occlusion ($t_b<t<t_c$) to the time $t_e$ where the inspiratory volume reaches a predetermined volume ($V(t_e)$) which may for example be ⅔ VT) to obtain an extrapolated airway pressure $P_{extr}(t_e)$;
e) subtracting the extrapolated airway pressure $P_{extr}(t_e)$ from the ventilator pressure $P_{aw}(t_e)$ to obtain an estimated driving pressure $P_{drv}(t_e)$;
f) calculating the resistive pressure $P_{res}(t_e)$ at the predetermined inspiratory volume (which as indicated, may for example be ⅔ VT) using the measured flow at that inspiratory volume and the resistance value determined in step a), and subtracting the resistive pressure $P_{res}(t_e)$ from the estimated driving pressure $P_{drv}(t_e)$, to determine the elastic pressure $P_{el}(t_e)$ and determining the elastance on the basis of the ratio of elastic pressure $P_{el}(t_e)$ to the predetermined inspiratory volume $V(t_e)$ (e.g., ⅔ VT).

In a preferred embodiment, the extrapolation of the time dependent airway pressure data is performed by fitting a predetermined function to the airway pressure data of the occlusion period and by obtaining the extrapolated pressure by calculating the fitted function at the extrapolation time where the inspiratory volume reaches a pre-determined value (e.g., ⅔ VT). For this extrapolation a predetermined linear, convex or concave function may be fitted to the pressure data of the occlusion period.

In a preferred embodiment, in the method for automatically determining the elastance E of the respiratory system, above-mentioned steps d) to f) are repeated for a sequence of pre-determined extrapolation volumes and a corresponding sequence of elastance values is determined. This sequence of elastance values, which shows a possible functional dependence of the calculated elastance on the extrapolation volume, is analyzed, and an elastance value is derived from a region of this function, where the dependence of the determined elastance values from the predetermined volume is lowest. This ensures that a reliable elastance value is determined from a region where it does not depend on the details of the extrapolation.

The methods of the present invention are conducted utilizing signal processing control units in a breathing apparatus which may be arranged and programmed to collect the sensed values of airway pressure, inspiratory volume and flow to record them as functions of time. The individual steps of the methods defined in the claims, in particular the fitting procedures for determining the transition, time in the time dependence of the flow V' may be implemented by computer algorithms in the control unit. Likewise the extrapolation procedure which is used to determine the elastance of the respiratory system may be implemented by programming the control unit with appropriate algorithms.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

DESCRIPTION OF THE PREFERRED EMBODIMENT

Figure 1:
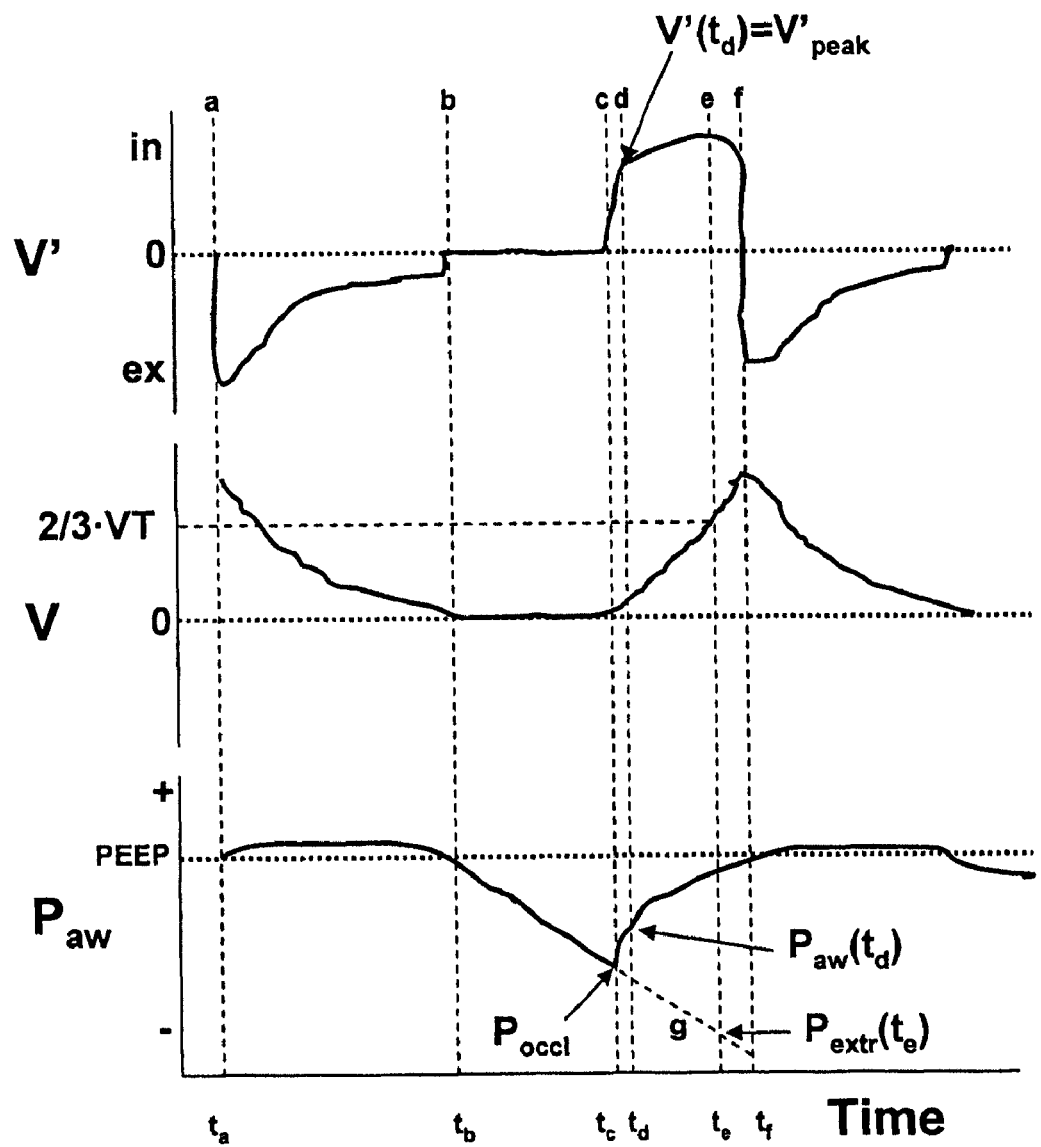
FIG. 1 is a graph showing the time dependencies of the measured airway pressure $P_{aw}$, the inspiratory volume V and the flow V' as a function of time, for a situation without assisted ventilation.

Referring to the drawings in particular, FIG. 1 shows a graph showing the time dependence of the airway pressure $P_{aw}$, inspiratory volume V and flow V'. By the dashed vertical lines, the following times are indicated: $t_a$=beginning of expiration, $t_b$=start of airway occlusion at the beginning of inspiration, $t_c$=release of airway occlusion, $t_d$=transition time, $t_e$=time when a predetermined part of the tidal volume has been reached (e.g., ⅔ VT), $t_f$=end of inspiration. g indicates the linear extrapolation of $P_{aw}(t)$ during the occlusion period to the entire tidal volume. $P^-_{mus}(t_e)=-P_{extr}(t_e)$ is the estimated pressure generated by the inspiratory muscles to generate a flow and volume at $t_e$. The designation in and ex on the vertical axis of V' indicate the inspiratory and expiratory flow portions.

After the end of the occlusion at $t_c$, the time dependence of the flow is analyzed to define the transition point where the first linear rise of high slope is transitioning to a further portion of lower slope. The resistance is calculated on the basis of a ratio of the estimated driving pressure $P^-_{drv}(t_d)=P_{aw}(t_d)+P^-_{mus}(t_d)=P_{aw}(t_d)-P_{extr}(t_d)$ (which is the difference between the transition time airway pressure $P_{aw}(t_d)$ and the extrapolated airway pressure during the occlusion $P_{extr}(t_d)$) to the transition time flow $V'(t_d)=V'_{peak}$. In case of short transition times (i.e. $t_d$-$t_c$ is small compared to $t_c$-$t_b$) then $P_{extr}(t_d)$ can be replaced by $P_{aw}(t_c)=P_{occl}$. $R=(P_{aw}(t_d)-P_{extr}(t_d))/V'_{peak} \approx (P_{aw}(t_d)-P_{occl})/V'_{peak}$.

According to this method, use is made of the consideration that the initial pressure at the end of the occlusion $P_{occl}$ with reference to the transition time airway pressure is an estimate of the real driving pressure $P_{drv}(t_d)$ which is responsible for the first linear rise of the flow to the value at the transition time $V'(t_d)=V'_{peak}$. In this part of the inspiration cycle, the inspiratory volume is still low and the relation between driving pressure $P_{drv}(t_d)$ and resulting initial flow at the transition time $V'_{peak}$ is dominated by the resistance of the respiratory system because effects of the elastance may still be neglected.

Directly after the occlusion period the driving pressure is purely resistive ($P_{drv}=P_{res}$), while with increasing volume during the breathing cycle the elastic pressure $P_{el}(t)$ rises while the resistive pressure $P_{res}(t)$ decreases, so that when the tidal volume VT is reached the resistive pressure dropped to zero and the entire muscular pressure $P_{mus}$ is counter-acting the elastic pressure $P_{el}$.

In connection with FIG. 1, the steps for a method of automatically determining the elastance of the respiratory system are now illustrated. First, the resistance of the respiratory system is determined by employing the above-described method. In addition to measuring flow and airway pressure as a function of time, the inspiratory volume is also monitored. Furthermore, the time dependence of the airway pressure during the occlusion period is recorded as a function of time, i.e. the rising (negative) pressure $P_{aw}$ between $t_b$ and $t_c$ (see respective dashed lines in FIG. 1). These time dependent airway pressure data are then utilized in an extrapolation step to determine the pressure at time $t_e$ at, which the inspiratory volume reaches the pre-determined volume, e.g., ⅔ of the ideal volume VT. The extrapolated airway pressure is designated as $P_{extr}(t_e)$ in FIG. 1.

Figure 2:
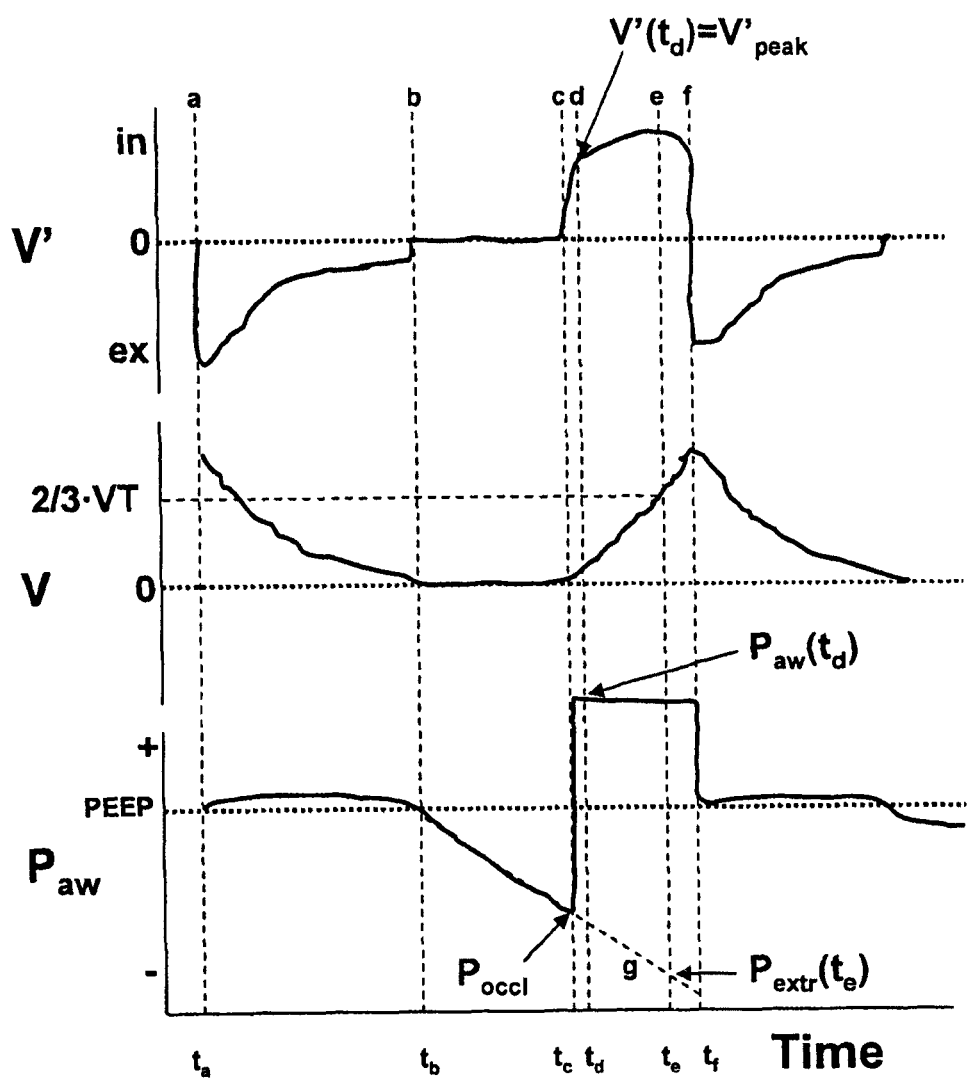
FIG. 2 is a graph as in FIG. 1 for a situation with assisted ventilation.

FIG. 2 shows a graph displaying the time dependence of the airway pressure $P_{aw}$, inspiratory volume V and flow V', as in FIG. 1 but for the case of assisted ventilation. Again, by the dashed vertical lines, the following times are indicated: $t_a$=beginning of expiration, $t_b$=start of airway occlusion at the beginning of inspiration, $t_c$=release of airway occlusion, $t_d$=transition time, $t_e$=time when a pre-determined part of the tidal volume has been reached (e.g., ⅔ VT), $t_f$=end of inspiration, and g indicates the linear extrapolation of $P_{aw}(t)$ during the occlusion period to the entire tidal volume. The absolute value of $P_{extr}(t_e)$ is the estimate of the pressure generated by the inspiratory muscles to generate a flow and volume at $t_e$.

Figure 3:
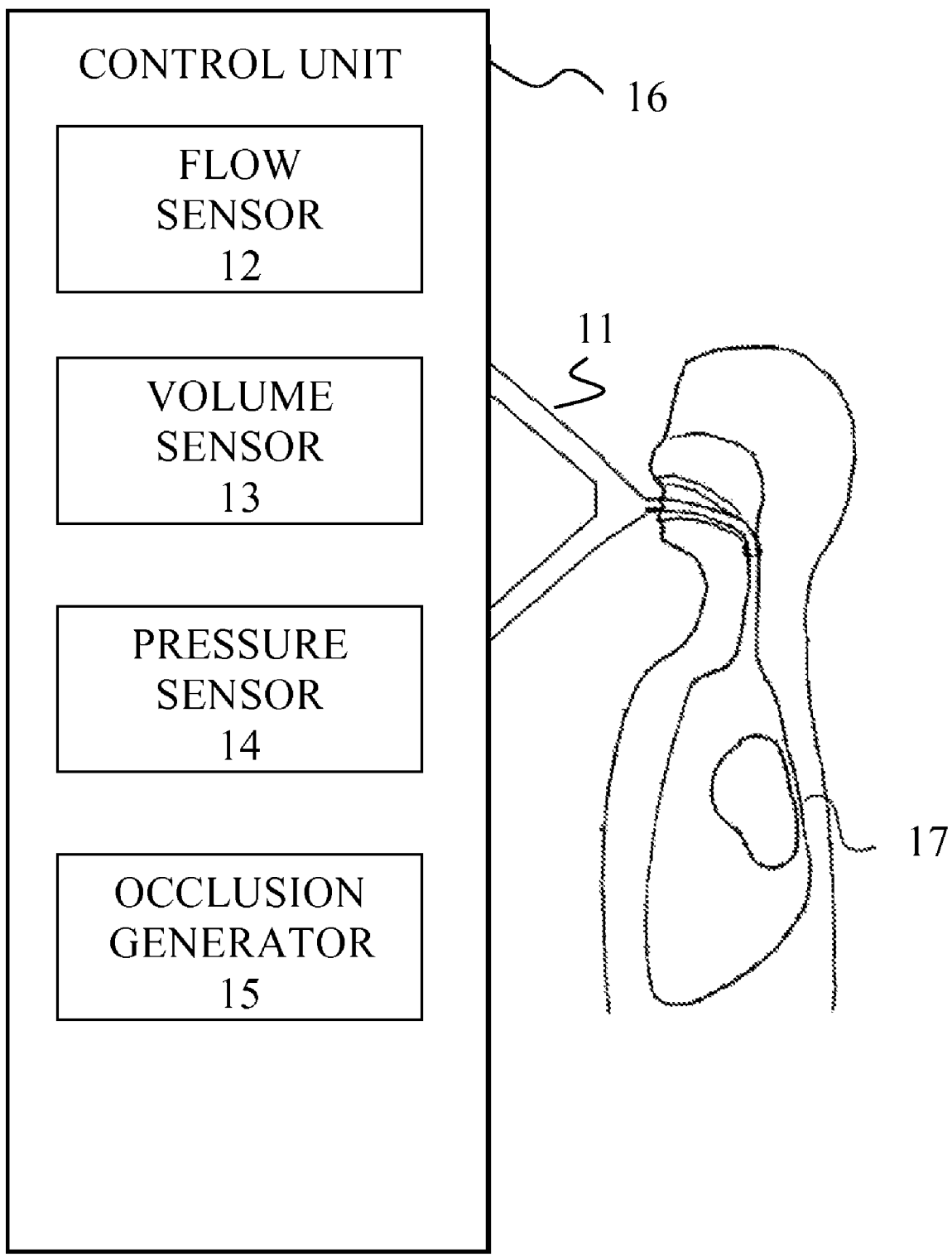
FIG. 3 is a schematic view of a patient connected to a breathing apparatus for performing the method of the present invention.

FIG. 3 shows a patient 17 connected to a breathing apparatus for performing the method of the present invention. The breathing apparatus includes an airway 11 and a control unit 16. The patient 23 breathes in and out through the airway 11. The control unit 16 includes a flow sensor 12 for measuring the flow through the airway 11, a volume sensor 13 for measuring the volume of breathing gas used by the patient 17, a pressure sensor 14 for measuring the pressure in the airway 11, and an occlusion generator 15 for generating an occlusion in the airway 11 for a predetermined period. The control unit 16 performs the calculations of the present invention based on the values measured by the sensor.

While a specific embodiment of the invention has been shown and described in detail to illustrate the application of the principles of the invention, it will be understood that the invention may be embodied otherwise without departing from such principles.

What is claimed is:

1. A method for automatically determining the resistance of the respiratory system of a spontaneously breathing intubated patient, wherein the method is conducted with or without assisted ventilation and includes an occlusion period at the start of inspiration, the method comprising:
   inhaling through a breathing apparatus;
   blocking a flow through the breathing apparatus at a start of said inhaling, said blocking being performed during the occlusion period;
   measuring flow (V') and airway pressure ($P_{aw}$) as a function of time;
   determining the airway pressure at the end of the occlusion period as end of occlusion airway pressure ($P_{aw}(t_c)=P_{occl}$);
   analyzing a time dependence of the flow starting at the end of the occlusion period to determine a transition time ($t_d$) at which the slope of the flow changes from a first high value to a second lower value, and/or analyzing a time dependence of the airway pressure starting at the end of the occlusion period to determine the transition time ($t_d$) at which the slope at the airway pressure changes from a first high value to a second lower value, or by detecting an increase of the airway pressure over a predetermined threshold value to determine the transition time ($t_d$);

determining the flow at the transition time as transition time flow ($V'(t_d)=V'_{peak}$) and determining the airway pressure at the transition time as transition time pressure ($P_{aw}(t_d)$);

calculating the resistance on the basis of the ratio of an estimated driving pressure at the transition time ($P_{drv}(t_d)$) and the transition time flow ($V'_{peak}$), wherein the value of the transition time driving pressure ($P_{drv}(t_d)$) is calculated as sum of the transition time airway pressure ($P_{aw}(t_d)$) and a muscular effort pressure ($P_{mus}(t_d)$) at the transition time, which muscular effort pressure ($P_{mus}(t_d)$) is extrapolated based on a predetermined time dependence of muscular effort pressure ($P_{mus}(t)$) during the occlusion period and based on value of the end of occlusion airway pressure ($P_{occl}$).

2. The method according to claim 1, wherein the predetermined time dependence is selected such that muscular effort pressure ($P_{mus}(t)$) is constant after the occlusion ($P_{mus}(t_d)=-P_{occl}$), and thus the extrapolated driving pressure is determined to be the transition time airway pressure less the occlusion airway pressure ($P_{drv}(t_d)=P_{aw}(t_d)-P_{occl}$).

3. A method according to claim 1, wherein the predetermined time dependence is selected such that muscular effort pressure ($P_{mus}(t)$) rises after the occlusion with constant slope (k) after the occlusion ($P_{mus}(t_d)=-P_{occl}+k^*(t_d-t_c)$), and thus the extrapolated driving pressure is determined to be transition time airway pressure less the occlusion airway pressure plus the constant ($P_{drv}(t_d)=P_{aw}(t_d)-P_{occl}+k^*(t_d-t_c)$).

4. The method according to claim 1, wherein the predetermined time dependence is selected such that muscular effort pressure $P_{mus}(t)$ proceeds after the occlusion with a curvature that is described by an $n^{th}$ order polynom ($P_{mus}(t_d)=-P_{occl}+k_1^*(t_d-t_c)+k_2^*(t_d-t_c)^2+k_3^*(t_d-t_c)^3+\ldots+k_n^*(t_d-t_c)^n$ and thus $P_{drv}(t_d)=P_{aw}(t_d)-P_{occl}+k_1^*(t_d-t_c)+k_2^*(t_d-t_c)^2+k_3^*(t_d-t_c)^3+\ldots+k_n^*(t_d-t_c)^n$).

5. The method according to claim 3, wherein the $P_{mus}(t_d)$ is corrected according to a-priori known pressure-flow characteristics of the respiratory muscles by applying a time dependent gain factor on the $P_{mus}$ signal.

6. The method according to claim 4, wherein $P_{mus}(t_d)$ is corrected according to the a-priori known pressure-flow characteristics of the respiratory muscles by applying a time dependent gain factor on the $P_{mus}$ signal.

7. The method according to claim 1, wherein the step of analyzing the time dependence of the flow data or the airway pressure data includes fitting of a predetermined non-linear function to the respective time-dependent data, said predetermined non-linear function having a first essentially linear portion and a second essentially linear portion with a smooth transition in between, wherein the slopes and lengths and the location of the smooth transition are determined by parameters which are varied in the fitting procedure.

8. The method according to claim 1, wherein the step of analyzing the time dependence of the flow or of the airway pressure data includes fitting two straight lines to respective the time-dependent data and determining the intersection of the two straight lines as the transition time value $t_d$.

9. The method according to claim 1, wherein said step of analyzing the time dependence of the flow data or the airway pressure data includes a linear filtering procedure of the respective time-dependent data in order to determine the change of slope point as the transition time value $t_d$.

10. A method for automatically determining the elastance (E) of the respiratory system of a spontaneously breathing intubated patient, wherein said method is conducted with or without assisted ventilation and includes an occlusion period at the start of inspiration, wherein said method comprises:

a) determining the resistance (R) of the respiratory system with or without assisted ventilation and including an occlusion period at the start of inspiration by:
inhaling through a breathing apparatus;
blocking a flow through the breathing apparatus at a start of said inhaling, said blocking being performed during the occlusion period;
measuring flow (V') and airway pressure ($P_{aw}$) as a function of time;
determining the airway pressure at the end of the occlusion period as end of occlusion airway pressure ($P_{aw}(t_c)=P_{occl}$);
analyzing a time dependence of the flow starting at the end of the occlusion period to determine a transition time ($t_d$) at which the slope of the flow changes from a first high value to a second lower value, and/or analyzing a time dependence of the airway pressure starting at the end of the occlusion period to determine the transition time ($t_d$) at which the slope at the airway pressure changes from a first high value to a second lower value, or by detecting an increase of the airway pressure over a predetermined threshold value to determine the transition time ($t_d$);
determining the flow at the transition time as transition time flow ($V'(t_d)=V'_{peak}$) and determining the airway pressure at the transition time as transition time pressure ($P_{aw}(t_d)$);
calculating the resistance on the basis of the ratio of an estimated driving pressure at the transition time ($P_{drv}(t_d)$) and the transition time flow ($V'_{peak}$), wherein the value of the transition time driving pressure ($P_{drv}(t_d)$) is calculated as sum of the transition time airway pressure ($P_{aw}(t_d)$) and a muscular effort pressure ($P_{mus}(t_d)$) at the transition time, which muscular effort pressure ($P_{mus}(t_d)$) is extrapolated based on a predetermined time dependence of muscular effort pressure ($P_{mus}(t)$) during the occlusion period and based on value of the end of occlusion airway pressure ($P_{occl}$);

b) measuring the inspiratory volume as a function of time;

c) determining the airway pressure ($P_{aw}(t)$) during the occlusion period ($t_b<t<t_c$) as a function of time ($P_{aw}(t)$);

d) extrapolating the airway pressure during the occlusion ($P_{aw}(t)$) with occlusion period ($t_b<t<t_c$) data to the time when the inspiratory volume reaches a predetermined volume ($t_e$) to obtain an extrapolated airway pressure ($P_{exfr}(t_e)$);

e) subtracting the extrapolated airway pressure ($P_{exfr}(t_e)$) from the ventilator pressure ($P_{aw}(t_e)$) to obtain an estimated driving pressure ($P_{drv}(t_e)$);

f) calculating the resistive pressure ($P_{res}(t_e)$) at the predetermined inspiratory volume ($\frac{2}{3}VT$) using the measured flow at that inspiratory volume and the resistance value determined in step a), and subtracting the resistive pressure ($P_{res}(t_e)$) from the estimated driving pressure ($P^-_{extr}(t_e)$) to determine the elastic pressure ($P_{el}(t_e)$), and determining the elastance on the basis of the ratio of elastic pressure ($P_{el}(t_e)$) to the predetermined inspiratory volume ($V(t_e)$).

11. The method according to claim 10, wherein said extrapolation of the time dependent airway pressure data is performed by fitting a predetermined function to the airway pressure data of the occlusion period and obtaining the extrapolated pressure by calculating the fitted function at the extrapolation time $t_e$ where the inspiratory volume reaches a predetermined value.

12. The method according to claim 11 wherein a predetermined linear convex or concave function is used in the fitting procedure for extrapolation.

13. The method according to claim 10, wherein:
steps d) to f) are repeated for a sequence of predetermined volumes ($x_i$–VT, $x_1 \ldots, x_N \leq 1$);
a corresponding sequence of elastance values ($E(x_i \cdot VT)$) is determined; and
an elastance value is selected from a region of the sequence where the dependence of the elastance from the predetermined volume is lowest.

14. The method according to claim 11, wherein:
steps d) to f) are repeated for a sequence of predetermined volumes ($x_i$–VT, $x_1 \ldots, x_N \leq 1$);
a corresponding sequence of elastance values ($E(x_i \cdot VT)$) is determined; and
an elastance value is selected from a region of the sequence where the dependence of the elastance from the predetermined volume is lowest.

15. The method according to claim 12, wherein:
steps d) to f) are repeated for a sequence of predetermined volumes ($x_i$–VT, $x_1 \ldots, x_N \leq 1$);
a corresponding sequence of elastance values ($E(x_i \cdot VT)$) is determined; and
an elastance value is selected from a region of the sequence where the dependence of the elastance from the predetermined volume is lowest.

16. The method according to claim 10, wherein the values for resistance (R) and elastance (E) as determined in a previous breathing cycle are used to calculate the muscular pressure (($P_{mus}$)), from the inspiratory volume (V) and flow (V') ($P_{mus} + P_{aw} = E \cdot V + R \cdot V'$, $P_{aw} = VA \cdot V + FA \cdot V'$) as a function of inspiratory volume to compare it to the extrapolated pressure value to check the extrapolation.

17. The method according to claim 11, wherein the values for resistance (R) and elastance (E) as determined in a previous breathing cycle are used to calculate the muscular pressure (($P_{mus}$)), from the inspiratory volume (V) and flow (V') ($P_{mus} + P_{aw} = E \cdot V + R \cdot V'$, $P_{aw} = VA \cdot V + FA \cdot V'$) as a function of inspiratory volume to compare it to the extrapolated pressure value to check the extrapolation.

18. The method according to claim 15, wherein the values for resistance (R) and elastance (E) as determined in a previous breathing cycle are used to calculate the muscular pressure (($P_{mus}$)), from the inspiratory volume (V) and flow (V') ($P_{mus} + P_{aw} = E \cdot V + R \cdot V'$, $P_{aw} = VA \cdot V + FA \cdot V'$) as a function of inspiratory volume to compare it to the extrapolated pressure value to check the extrapolation.

19. A method for determining a resistance of a respiratory system of a patient, the method comprising the steps of:
inhaling through a breathing apparatus;
blocking a flow through the breathing apparatus at a start of said inhaling, said blocking being performed during an occlusion period;
measuring flow through the breathing apparatus during said inhaling as a function of time;
measuring airway pressure in the breathing apparatus during said inhaling as a function of time;
determining the airway pressure at an end of the occlusion period ($P_{occl}$);
determining a transition time ($t_d$) during said inhaling and after the occlusion period, the transition time being determined by one of,
determining a time when a slope of the flow changes from a first high value to a second lower value,
determining a time when a slope of the airway pressure changes from a first high value to a second lower value, and
determining a time when the airway pressure increases above a predetermined threshold;
determining the flow at the transition time $t_d$ as $V'_{peak}$;
determining the airway pressure at the transition time $t_d$ as $P_{aw}(t_d)$;
determining muscular pressure at the transition time ($P_{mus}(t_d)$) by extrapolation of the airway pressure during the occlusion period;
calculating a driving pressure at the transition time ($P_{drv}(t_d)$) by adding $P_{aw}(t_d)$ and $P_{mus}(t_d)$;
calculating the resistance of the respiratory system based on a ratio of $P_{drv}(t_d)$ to $V'_{peak}$.

* * * * *